United States Patent
Nomura et al.

(10) Patent No.: US 11,771,881 B2
(45) Date of Patent: Oct. 3, 2023

(54) NEEDLE ADAPTER AND DEVICE FOR SOFT MATERIAL EXTRUSION OF CORE-SHELL STRUCTURES

(71) Applicant: Toyota Motor Engineering & Manufacturing North America, Inc., Plano, TX (US)

(72) Inventors: Tsuyoshi Nomura, Novi, MI (US); Minoru Hirano, Cambridge, MA (US)

(73) Assignee: Toyota Motor Engineering & Manufacturing North America, Inc., Plano, TX (US)

( * ) Notice: Subject to any disclaimer, the term of this patent is extended or adjusted under 35 U.S.C. 154(b) by 960 days.

(21) Appl. No.: 16/555,106

(22) Filed: Aug. 29, 2019

(65) Prior Publication Data
US 2021/0060328 A1   Mar. 4, 2021

(51) Int. Cl.
| | |
|---|---|
| *B29C 48/09* | (2019.01) |
| *A61M 39/10* | (2006.01) |
| *A61M 5/32* | (2006.01) |
| *B29C 48/00* | (2019.01) |
| *B29C 48/335* | (2019.01) |
| *B29C 48/25* | (2019.01) |

(Continued)

(52) U.S. Cl.
CPC .......... *A61M 39/10* (2013.01); *A61M 5/3297* (2013.01); *B29C 48/02* (2019.02);
(Continued)

(58) Field of Classification Search
CPC ............... A61M 39/10; A61M 5/3297; A61M 2005/3201; A61M 2039/1077;
(Continued)

(56) References Cited

U.S. PATENT DOCUMENTS 4,740,205 A * 4/1988 Seltzer ............. A61B 5/150587
604/192
6,488,666 B1* 12/2002 Geist .................. A61M 5/3213
604/263

(Continued)

FOREIGN PATENT DOCUMENTS

| | | |
|---|---|---|
| EP | 1874784 B1 | 8/2009 |
| EP | 2016907 B1 | 4/2011 |
| WO | 2018078130 A1 | 5/2018 |

OTHER PUBLICATIONS

Cao, Q. et al., "Coaxial nozzle-assisted 3D bioprinting with built-in microchannels for nutrients delivery," Biomaterials 61 (2015) pp. 203-215.

(Continued)

*Primary Examiner* — Galen H Hauth
*Assistant Examiner* — Shibin Liang
(74) *Attorney, Agent, or Firm* — Christopher G. Darrow; Darrow Mustafa PC

(57) ABSTRACT

A two piece adapter for extrusion of cylindrical core-shell structures using conventional biomedical needles includes first and second adapter pieces. The first adapter piece includes first and second (core and shell) inlet ports. The core inlet port leads directly to a male Luer fitting attachable to a core needle and surrounded by a threaded chamber. The shell inlet port is led, via a side chamber, into the side of the threaded chamber. The second adapter piece attaches to the bottom of the threaded chamber and is configured to attach to a shell needle, so that the shaft of the core needle sits inside the shaft of the shell needle.

20 Claims, 13 Drawing Sheets

(51) Int. Cl.
*B29C 48/02* (2019.01)
*B29C 48/21* (2019.01)

(52) U.S. Cl.
CPC ............ *B29C 48/022* (2019.02); *B29C 48/09* (2019.02); *B29C 48/21* (2019.02); *B29C 48/2566* (2019.02); *B29C 48/335* (2019.02); *A61M 2005/3201* (2013.01); *A61M 2039/1077* (2013.01); *B29K 2089/00* (2013.01)

(58) Field of Classification Search
CPC .... A61M 5/00; B29C 48/022; B29C 48/2566; B29C 48/09; B29C 48/02; B29C 48/21; B29C 48/335; B29K 2089/00; A61K 9/70; A61K 9/48; A61K 9/4808
See application file for complete search history.

(56) References Cited

U.S. PATENT DOCUMENTS

| | | | |
|---|---|---|---|
| 8,419,722 B2 | 4/2013 | Richards et al. | |
| 10,780,059 B2 * | 9/2020 | Edirisinghe | A61K 9/4891 |
| 2004/0247867 A1 | 12/2004 | Chaouk et al. | |
| 2010/0145265 A1 * | 6/2010 | Min | A61M 25/1011 604/95.03 |
| 2016/0228611 A1 | 8/2016 | Castro et al. | |
| 2016/0375223 A1 * | 12/2016 | Avneri | A61B 5/150748 600/581 |
| 2019/0008998 A1 | 1/2019 | Cui et al. | |

OTHER PUBLICATIONS

Cole-Parmer Instrument Company,LLC, "Cole-Parmer Male-female large-bore adapter, radiation-stable polycarbonate, pack of 25," Item #EW-45509-91, (https://www.coleparmer.com/i/cole-parmer-male-female-large-bore-adapter-radiation-stable-polycarbonate-pack-of-25/4550991?searchterm=EW-45509-91) last downloaded Jul. 19, 2019 (2 pages).

Gesim, "Artificial Tissue from Maccaroni Strands" (https://gesim-bioinstruments-microfluidics.com/coreshell-extruder/) last downloaded Jul. 15, 2019 (2 pages).

Jia, W. et al., "Direct 3D bioprinting of perfusable vascular constructs using a blend bioink," Biomaterials 106 (2016) pp. 58-68.

* cited by examiner

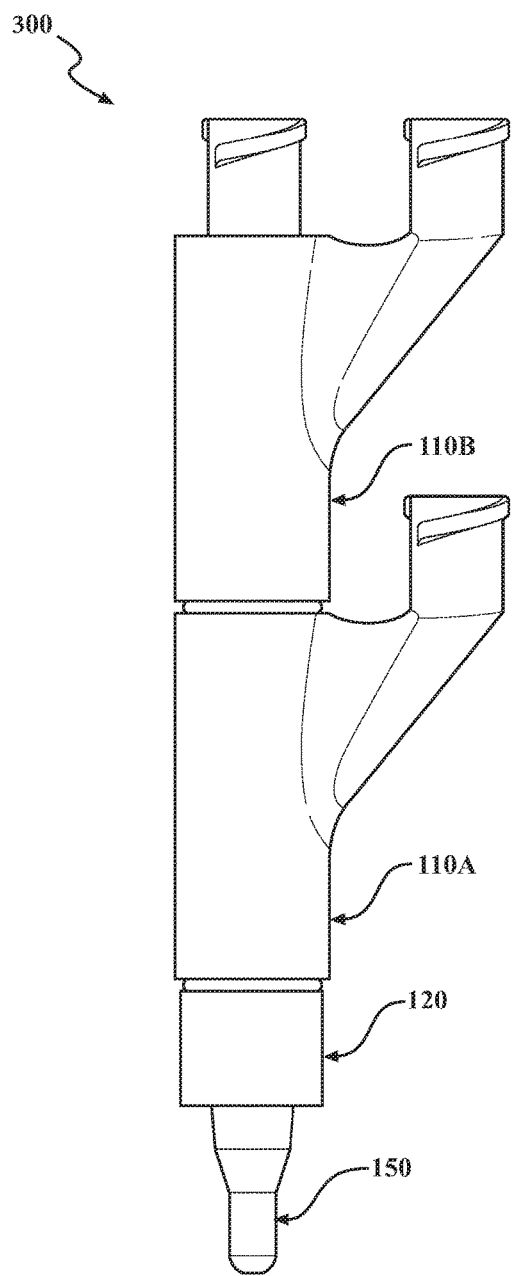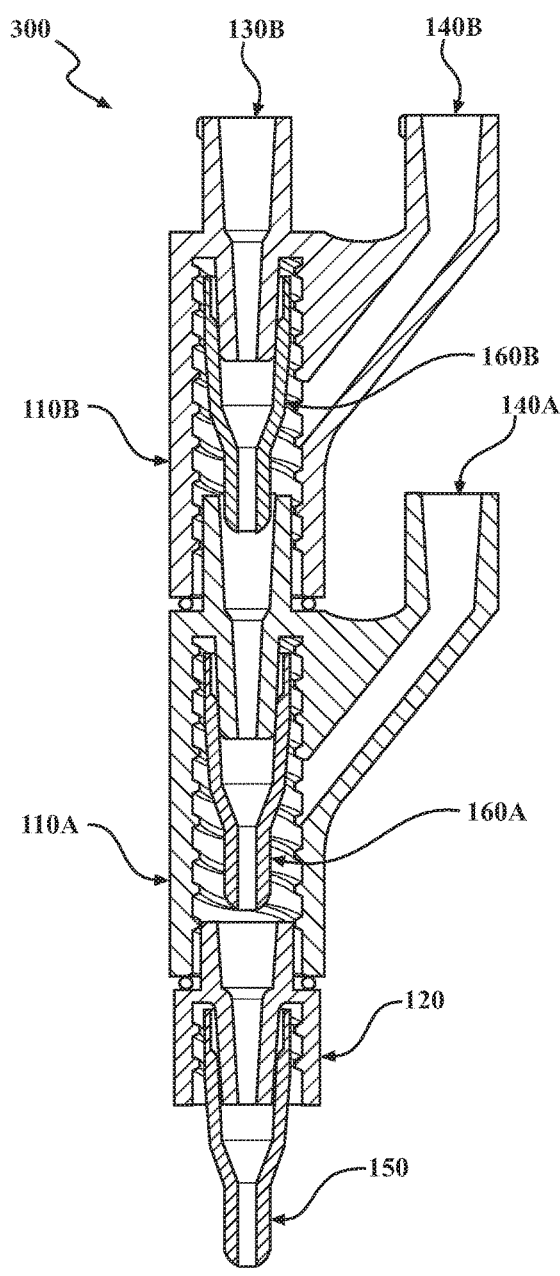
FIG. 7A
FIG. 7B

NEEDLE ADAPTER AND DEVICE FOR SOFT MATERIAL EXTRUSION OF CORE-SHELL STRUCTURES

TECHNICAL FIELD

The present disclosure generally relates to adapters for biomedical needles and, more particularly, to adapters for extrusion of core-shell tubular structures.

BACKGROUND

The background description provided herein is for the purpose of generally presenting the context of the disclosure. Work of the presently named inventors, to the extent it may be described in this background section, as well as aspects of the description that may not otherwise qualify as prior art at the time of filing, are neither expressly nor impliedly admitted as prior art against the present technology.

Soft tubular structures and other soft cylindrical core-shell structures have many important roles in industry and biomedical applications. For example, artificial perfusable tissues and prosthetics can require artificial vasculature to supply nutrients. Such structures can be difficult to make, however, particularly with the necessary reproducibility and biocompatibility.

In some instances, researchers seeking to fabricate such core-shell structures have made their own extrusion devices using biomedical needles. Such rudimentary devices generally involve boring a hole in the hub of a first needle, inserting the shaft of a second needle into the hole and sealing the juncture with an adhesive, and inserting the shaft of the first needle into the shaft of a third needle. Such makeshift devices typically suffer from multiple defects, including: possibility of injury while making the device; lack of reproducible results, and introduction of materials contrary to the intended function, such as non-biocompatible adhesives; and need to cut the coaxial needle shafts to obtain co-terminal tips.

In other instances, pre-fabricated core-shell nozzle systems are commercially available. Such devices tend to be expensive, they are not customizable (e.g. a single unit is capable of extruding only a single core-shell dimension), and the nozzles can easily be clogged with extrusion material, such as bioink. For all of these reasons, such systems are in limited use, especially among researchers.

Accordingly, it would be desirable to provide an improved device for extrusion of core-shell structures.

SUMMARY

This section provides a general summary of the disclosure, and is not a comprehensive disclosure of its full scope or all of its features.

In various aspects, the present teachings provide an adapter for extruding core-shell structures with two needles. The adapter includes a first adapter piece and a second adapter piece. The first adapter piece includes a body having an internal threaded chamber with first and second opposite ends, the first opposite end comprising an open threaded end configured to couple with a female Luer fitting, and the second opposite end comprising an internal male Luer fitting. The first adapter piece also includes a first inlet port comprising an external female Luer fitting configured to pass a first inlet fluid directly to the internal male Luer fitting. The first adapter piece further includes a second inlet port comprising an external female Luer fitting configured to pass a second inlet fluid into the internal threaded chamber via a side channel. The adapter additionally includes a second adapter piece having a female Luer fitting configured to couple with the open end of the internal threaded channel, and a male Luer fitting configured to couple with a needle. The male Luer fitting extends coaxially from the female Luer fitting.

In other aspects, the present teachings provide a device for extruding core-shell tubular structures. The device includes a core fluid pathway having a first inlet port on a first adapter piece. The first inlet port is configured to receive core fluid from an external source. The core fluid pathway also includes a first tapered male Luer fitting on the first adapter piece and a core needle attached to the first tapered male Luer fitting and in fluid communication with the first inlet port. The device further includes a shell fluid pathway having a cylinder with a threaded internal chamber surrounding the first tapered male Luer fitting, and a second inlet port atop the side channel. The shell fluid pathway further includes a second adapter body having a female Luer fitting, reversibly attached to the threaded internal chamber, and a second tapered male Luer fitting in direct fluid communication with the female Luer fitting. The shell fluid pathway also includes a shell needle connected to the second male Luer fitting, and in fluid communication with the second inlet port, such that the core and shell needles are coaxial.

In still other aspects, the present teachings provide a device for extruding core-shell structures with two needles. The device includes a first adapter piece and a second adapter piece. The first adapter piece includes a body having an internal threaded chamber with first and second opposite ends, the first opposite end comprising an open threaded end configured to couple with a female Luer fitting, and the second opposite end comprising an internal male Luer fitting. The first adapter piece also includes a first inlet port comprising an external female Luer fitting configured to pass a first inlet fluid directly to the internal male Luer fitting. The first adapter piece further includes a second inlet port comprising an external female Luer fitting configured to pass a second inlet fluid into the internal threaded chamber via a side channel. The adapter additionally includes a second adapter piece having a female Luer fitting configured to couple with the open end of the internal threaded channel, and a male Luer fitting configured to couple with a needle. The male Luer fitting extends coaxially from the female Luer fitting. The device also includes a core needle connected to the internal male Luer fitting of the first adapter piece, and a shell needle connected to the male Luer fitting of the second adapter piece.

Further areas of applicability and various methods of enhancing the above coupling technology will become apparent from the description provided herein. The description and specific examples in this summary are intended for purposes of illustration only and are not intended to limit the scope of the present disclosure.

BRIEF DESCRIPTION OF THE DRAWINGS

The present teachings will become more fully understood from the detailed description and the accompanying drawings, wherein:

FIGS. 7A and 7B are a side plan view and a side sectional view, respectively, of an alternative variation of a device for extrusion of core-mid-shell structures, the adapter having two copies of the first adapter piece stacked to form two concentric cores.

It should be noted that the figures set forth herein are intended to exemplify the general characteristics of the methods, algorithms, and devices among those of the present technology, for the purpose of the description of certain aspects. These figures may not precisely reflect the characteristics of any given aspect, and are not necessarily intended to define or limit specific embodiments within the scope of this technology. Further, certain aspects may incorporate features from a combination of figures.

DETAILED DESCRIPTION

The present teachings provide devices for extruding core-shell structures, and adapters for making such devices. The adapters accept common biomedical needles, thereby converting an adapter of the present teachings into an extrusion device. The provided adapters enable extrusion of two different concentric layers of soft materials, in a coaxial manner, from two different material supply sources (e.g. syringes, bags, containers, or tubes).

Adapters of the present teachings include reversibly connectible components. The first component has at least two entry ports and connects to a needle having a relatively long, narrow shaft. This needle then becomes the core needle, for extruding the core portion of the eventual core-shell structure. The second adapter component connects to a needle having a relatively short, wide shaft. This needle then becomes the shell needle, for extruding the shell portion of the eventual core-shell structure. The first and second adapter components connect together to form the core-shell extrusion device. In the completed device, one of the entry ports is in fluid communication with the core needle and the other entry port is in fluid communication with the shell needle. The core needle shaft is sheathed within the shell needle shaft so that liquid passed into the first entry port is extruded as core material and liquid passed into the second entry port is extruded as shell material, the core and shell materials together forming a core-shell tubular structure.

Figure 1:
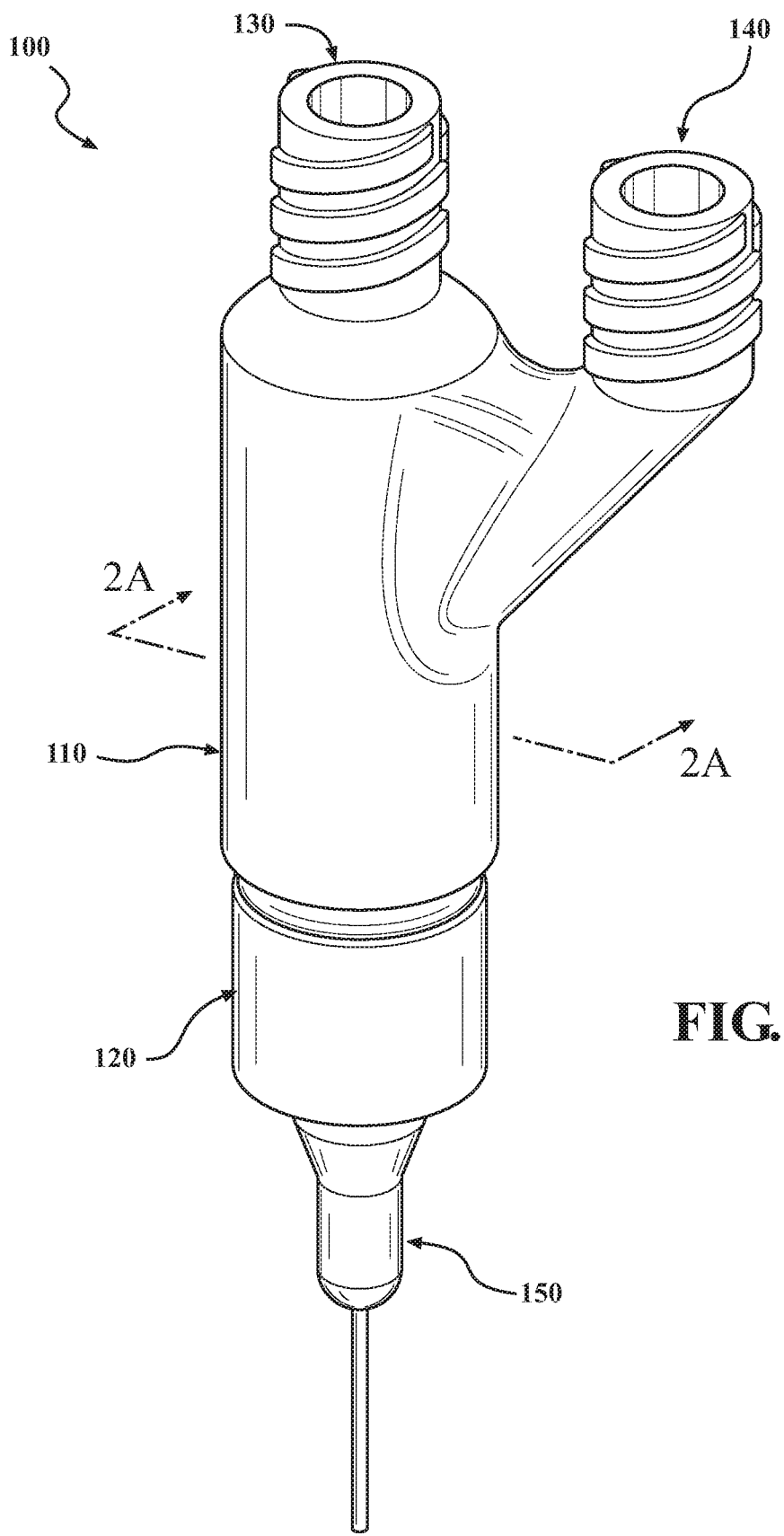
FIG. 1 is a perspective view of a device of the present teachings for extruding core-shell structures.

FIG. 1 shows a perspective view of a device 100 for extruding a core-shell structure. As used herein, the expression "core-shell structure" refers to a structure of concentric, or coaxial cylinders, having an outer, or shell, cylinder and an inner, or core, cylinder. In some implementations, the core cylinder can consist of air, so that the core-shell structure is a hollow tube. It will be understood that in many implementations, the core and shell cylinders of the core-shell structure can be flexible and/or non-linear along their shared axis.

Figure 2A:
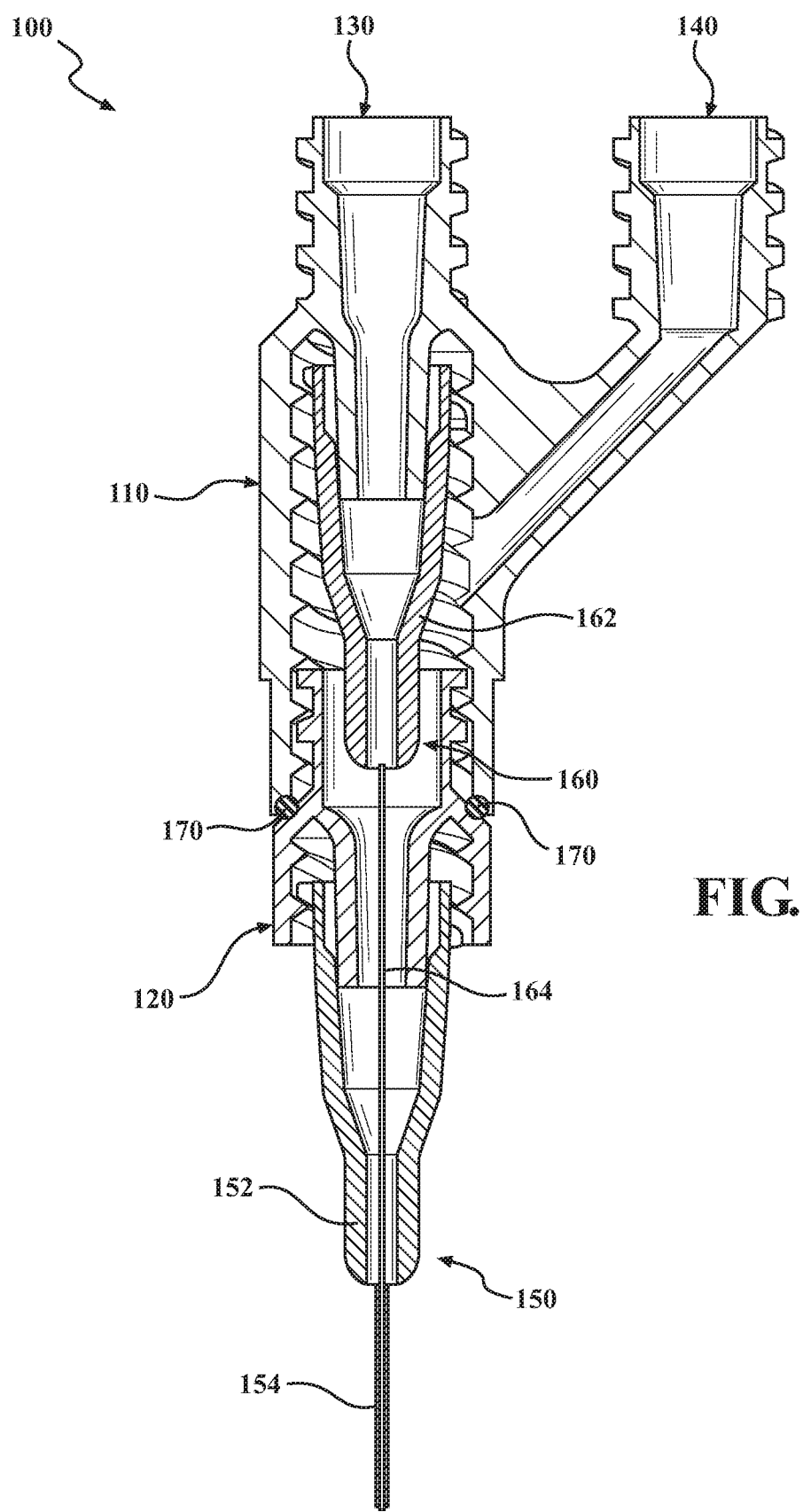
FIG. 2A side cross-sectional view of the device of FIG. 1, viewed along the line 2A-2A, and including two needles.
Figure 2B:
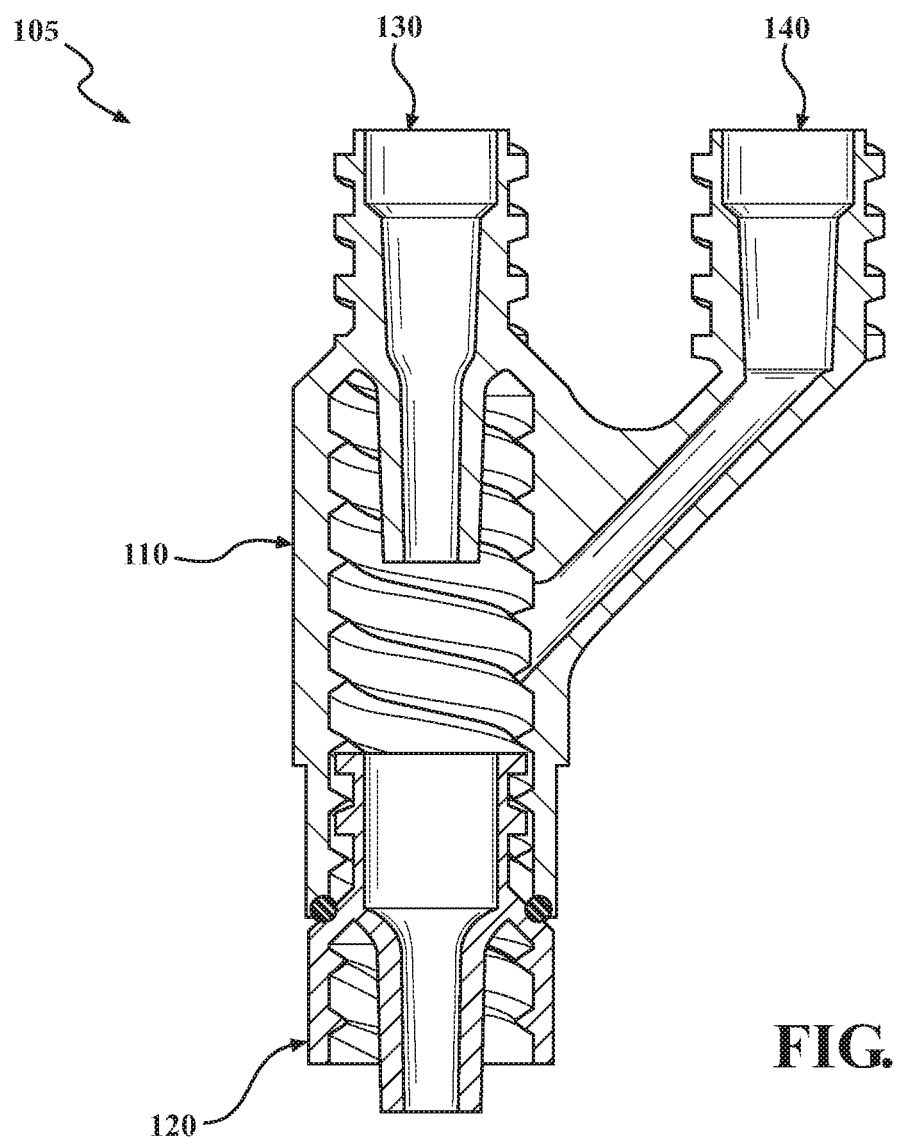
FIG. 2B is a side cross-sectional view of a two-piece adapter for making the device of FIGS. 1 and 2A via attachment of two needles.

FIG. 2A shows a side cross-sectional view of the device 100 of FIG. 1, viewed along the line 2-2, illustrating a shell needle 150 and a core needle 160 largely contained within the device 100 interior. FIG. 2B shows an adapter 105 of the present teachings, viewed along the same viewing axis as the device in FIG. 2A. The adapter 105 includes a first adapter piece 110 and a second adapter piece 120. It will be noted that the device 100 of FIG. 2A includes the adapter 105 of FIG. 2B, as well as the core and shell needles 150, 160. The second adapter piece 120 is configured to reversibly attach to the shell needle 150. The first adapter piece has inlet ports 130, 140 and is configured to reversibly attach to the core needle 160.

Figure 2C:
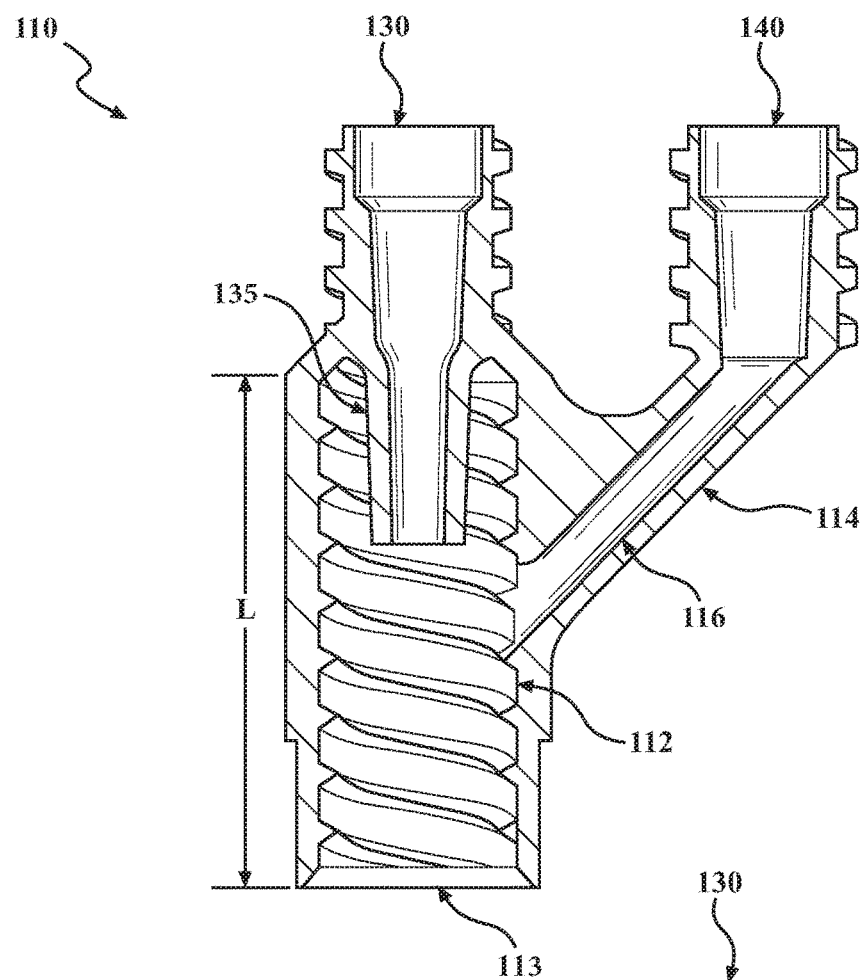
FIG. 2C is a side cross-sectional view of a first, "upper" piece of the two-piece adapter of FIG. 2B.
Figure 2D:
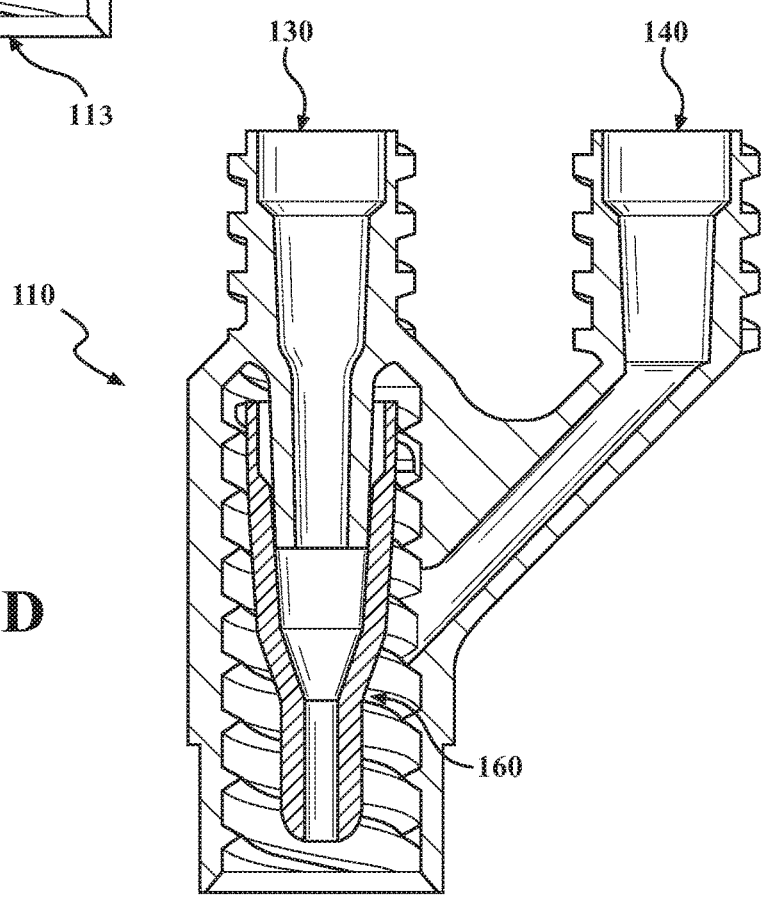
FIG. 2D is a side cross-sectional view of the first piece of FIG. 2C with a core needle attached.
Figure 2E:
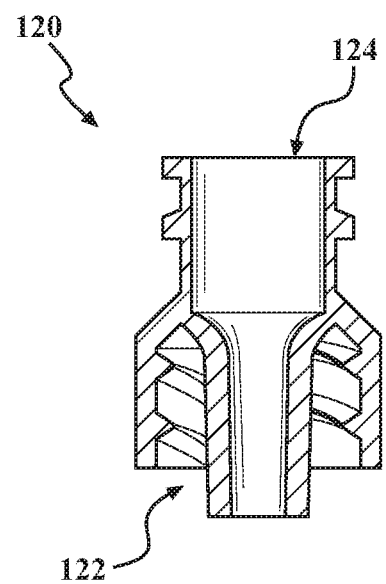
FIG. 2E is a side cross-sectional view of a second, "lower" piece of the two-piece adapter of FIG. 2B.
Figure 2F:
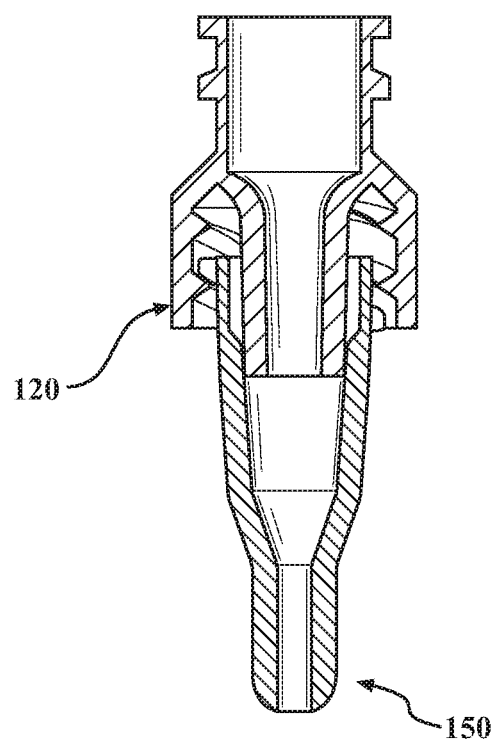
FIG. 2F is a side cross-sectional view of the lower piece of FIG. 2E with a shell needle attached.
Figure 2G:
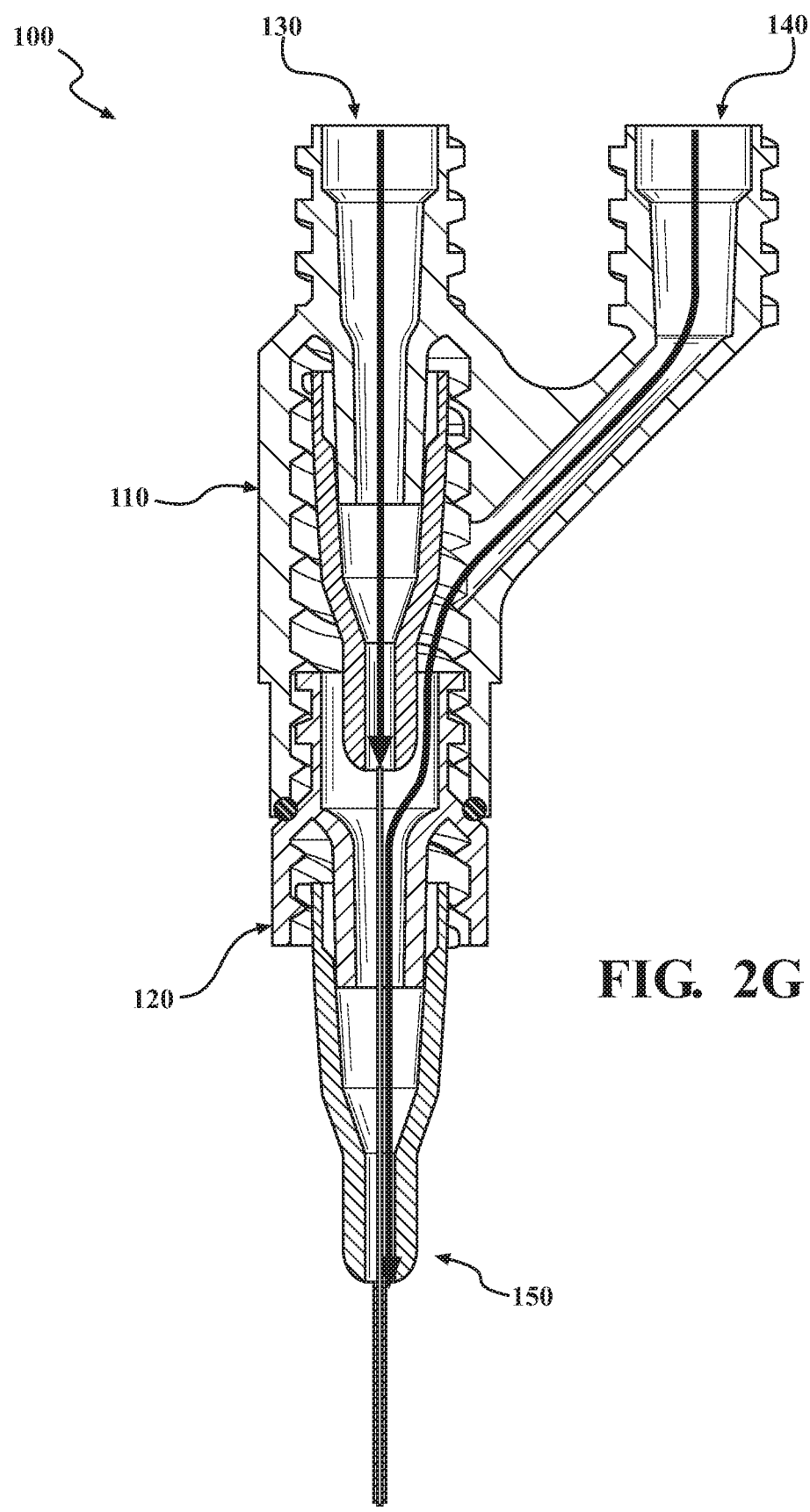
FIG. 2G is the side cross-sectional view of FIG. 2A, with block arrows showing a flow path of shell liquid.

FIGS. 2C and 2D show side cross-sectional views of the first adapter piece 110, without and with the core needle 160 attached, respectively. FIGS. 2E and 2F show side cross-sectional views of the second adapter piece 120, without and with the shell needle 150 attached, respectively. FIG. 2G shows the side cross-sectional view of FIG. 2A, with curvilinear block arrows illustrating a generalized flow path of uncured core and shell liquid during extrusion.

Referring particularly to FIGS. 2A-2F, the second adapter piece 120 includes a male Luer fitting 122 and a female Luer fitting 124 opposite to, and in fluid communication with, the male Luer fitting 122. The male Luer fitting is configured to dock with the hub 152 of the shell needle 150.

The first adapter piece 110 includes a core inlet port 130 and a shell inlet port 140. In certain implementations, either or both of the core inlet port 130 and the shell inlet port 140 can include a female Luer fitting, configured to dock with a male Luer fitting of a syringe. It will be noted that in the examples of FIGS. 1 and 2A-2C, both inlet ports 130, 140 include female Luer fittings. In some instances, either or both of the core inlet port 130 and the shell inlet port 140 can include a tube fitting, such as a barbed tube fitting or a compression tube fitting. In certain implementations, the either or both of the core inlet port 130 and the shell inlet port 140 can include a tapered female Luer fitting of the type shown in FIGS. 1, 2A-2D, and 2G, and can be reversibly attached to Luer tube fittings that have a male Luer fitting opposite a barbed or other tube fitting.

The core inlet port 130 is in fluid communication with a male Luer fitting 135 that is located internally in the first adapter piece 110, with an internal threaded chamber 112. The internal threaded chamber is bounded by an open end 113 and the male Luer fitting 135, residing at the opposite end of the internal threaded chamber 112 from the open end 113. The open end 113 and the male Luer 135 fitting can be separated by the distance L. The male Luer fitting 135 of the first adapter piece 110 is configured to couple with a core needle 160. Thus, when a core needle 160 is attached, the core inlet port 130, male Luer adapter 135 of the first adapter piece 110, and the core needle 160 are in fluid communication one another, and form a pathway through which uncured core fluid can transit the device 100. While the internal threaded chamber 112 is threaded along its entire length, L, in the example of FIGS. 2A-2G, it need not necessarily be so, but could be threaded at its ends around the open end 113 and around the male Luer fitting 135.

The open end 113 of the internal threaded chamber 112 of the first adapter piece 110 is configured to couple with the female Luer fitting 124 of the second adapter piece 120. It will be noted that when the first and second adapter pieces 110, 120 are attached via coupling of the open end 113 and the female Luer fitting 124 of the second adapter piece 120, the adapter 100 is assembled. The assembled adapter 105 or device 100 can include an O-ring 170 at the junction between the first and second adapter pieces 110, 120, to ensure a liquid-proof seal.

The shell inlet port 140 of the first adapter piece is in fluid communication with the internal threaded chamber 112 via a side channel 116. In the example of FIGS. 2A-2G, the side channel 116 is contained within side arm 114. In general, the shell inlet port 140, side channel 116, and internal threaded chamber 112 form a fluid pathway that is parallel to the pathway through which uncured core fluid can transit that is formed by the core inlet port 130, male Luer adapter 135 of the first adapter piece 110, and the core needle 160

Figure 3:
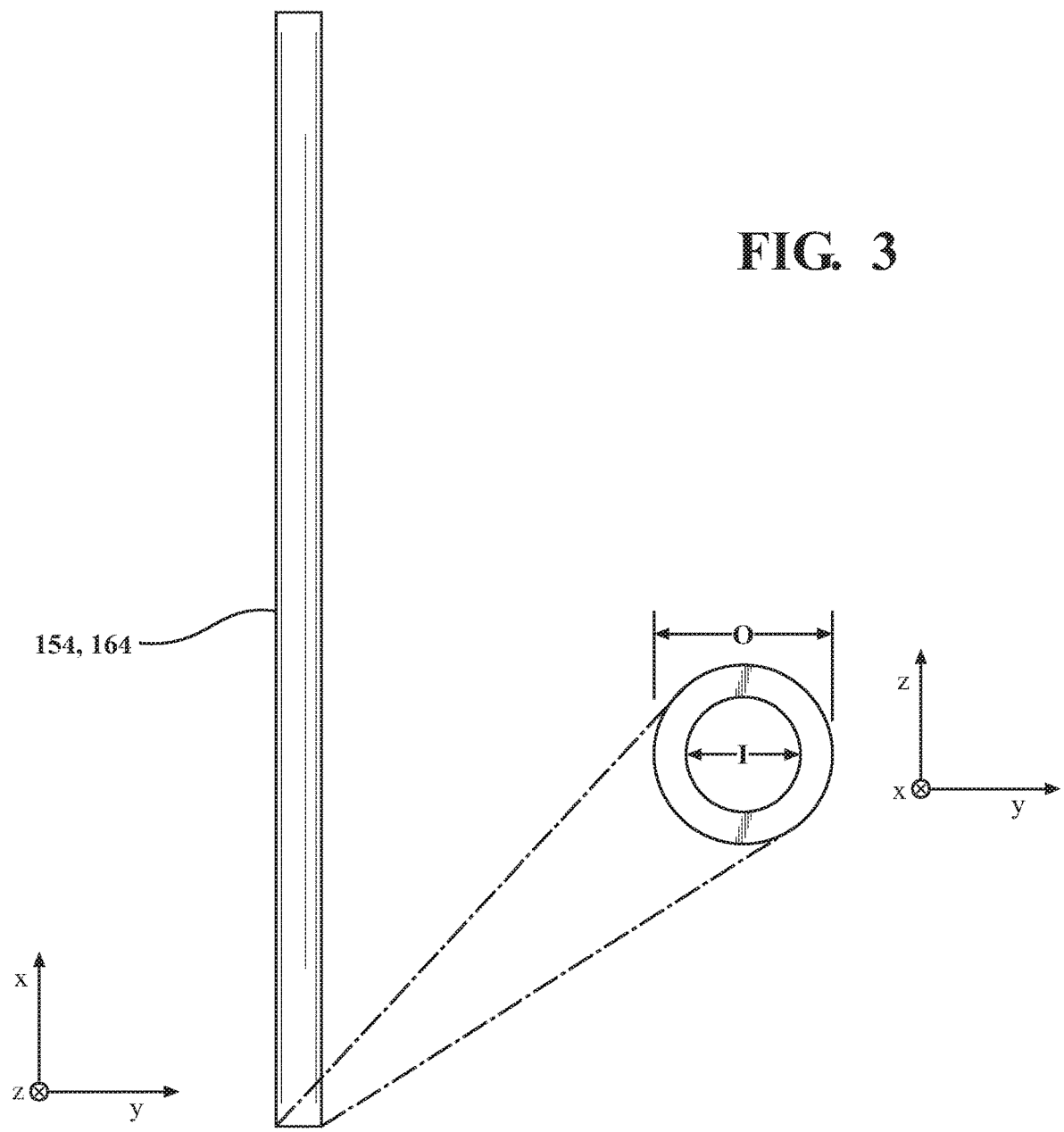
FIG. 3 is a side plan view of a needle shaft, with an expanded end-on view of a needle tip.

FIG. 3 shows a side plan view of a needle shaft, with an inset end plan view of the tip of the needle shaft, indicating that the needle shaft has an inner diameter, I, and an outer diameter, O. With particular reference to FIGS. 2A and 3, the core needle 160 includes a hub 162 and a shaft 164. It will be understood that the hub 162 is conventionally, but not necessarily, formed of plastic and includes a female Luer fitting whereby it is reversibly locked to the male Luer fitting 135 of the first adapter piece 110. It will further be understood that the shaft is conventionally, but not necessarily, formed of stainless steel and defines a tube having a cross-sectional inner diameter and a cross-sectional outer diameter, as shown in FIG. 3.

The shell needle 150 includes a hub 152 and a shaft 154. It will be understood that the hub 152 is conventionally, but not necessarily, formed of plastic and includes a female Luer fitting whereby it is reversibly locked to the male Luer fitting 122 of the second adapter piece 120. It will further be understood that the shaft is conventionally, but not necessarily, formed of stainless steel and defines a tube having a cross-sectional inner diameter and a cross-sectional outer diameter, as shown in FIG. 3. It will be noted that, in FIGS. 2D and 2F, the needle shafts 154, 164 are omitted for simplicity, and only the needle hubs 152, 162 are shown.

As shown in FIGS. 2A and 2G, when the device 100 is fully formed with first and second adapter pieces 110, 120 coupled together along with core and shell needles 150, 160 as described above, the shaft 154 of the core needle 150 is nested inside the shaft 164 of the core needle 160, forming a coaxial pair of needle shafts. It will therefore be appreciated that the outer diameter of the shaft 164 of the core needle 160 should be less than the inner diameter of the shaft 154 of the shell needle 150. It can further be seen, with particular reference to FIG. 2G, that in the fully assembled device 100, the core inlet port 130 is in fluid communication with the shaft 164 of the core needle 160, and the shell inlet port 140 is in fluid communication with the shaft 154 of the shell needle 150.

Thus, when an uncured core fluid is propelled into the core entry port 130, it proceeds directly to the core needle 160 and through the core needle shaft 164, as shown in FIG. 2G. Similarly, when an uncured shell fluid is propelled in the shell entry port 140, it proceeds through the side channel 116, into the internal threaded channel 112, further into the hub 152 of the shell needle 150, and transits the shaft 154 of the shell needle 150. When uncured core fluid and uncured shell fluid are simultaneously propelled into their respective entry ports 130, 140, they will transit the device as discussed and shown partially in FIG. 2G, and extrude from the tips of their respective needle shafts 160, 150 in the desired core-shell configuration.

It will be appreciated that a user can easily change the dimensions of the core-shell extrudate by changing the gauges of sizes of the core and shell needles 160, 150. It is only necessary, as mentioned above, that the inner diameter of the shaft 154 of the shell needle 150 be greater than the outer diameter of the shaft 164 of the core needle 160. As also mentioned above, the shaft 164 of the core needle 160 should generally be longer than the shaft 154 of the shell needle 150, so that the tips of the two shafts 154, 164 are approximately coincident (i.e. the needle shafts 154, 164 end at approximately the same place).

Figure 4A:
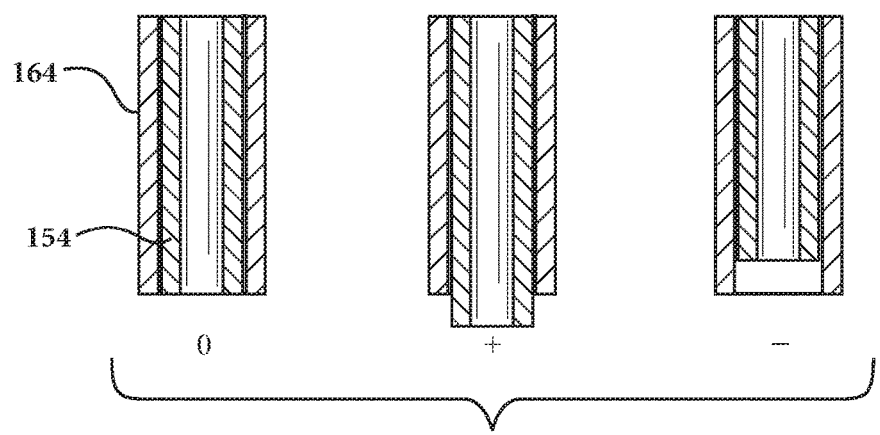
FIG. 4A is a side cross-sectional view of end portions of three needle shafts pairs showing neutral, positive, and negative offset between the concentric core and shell needles.
Figure 4B:
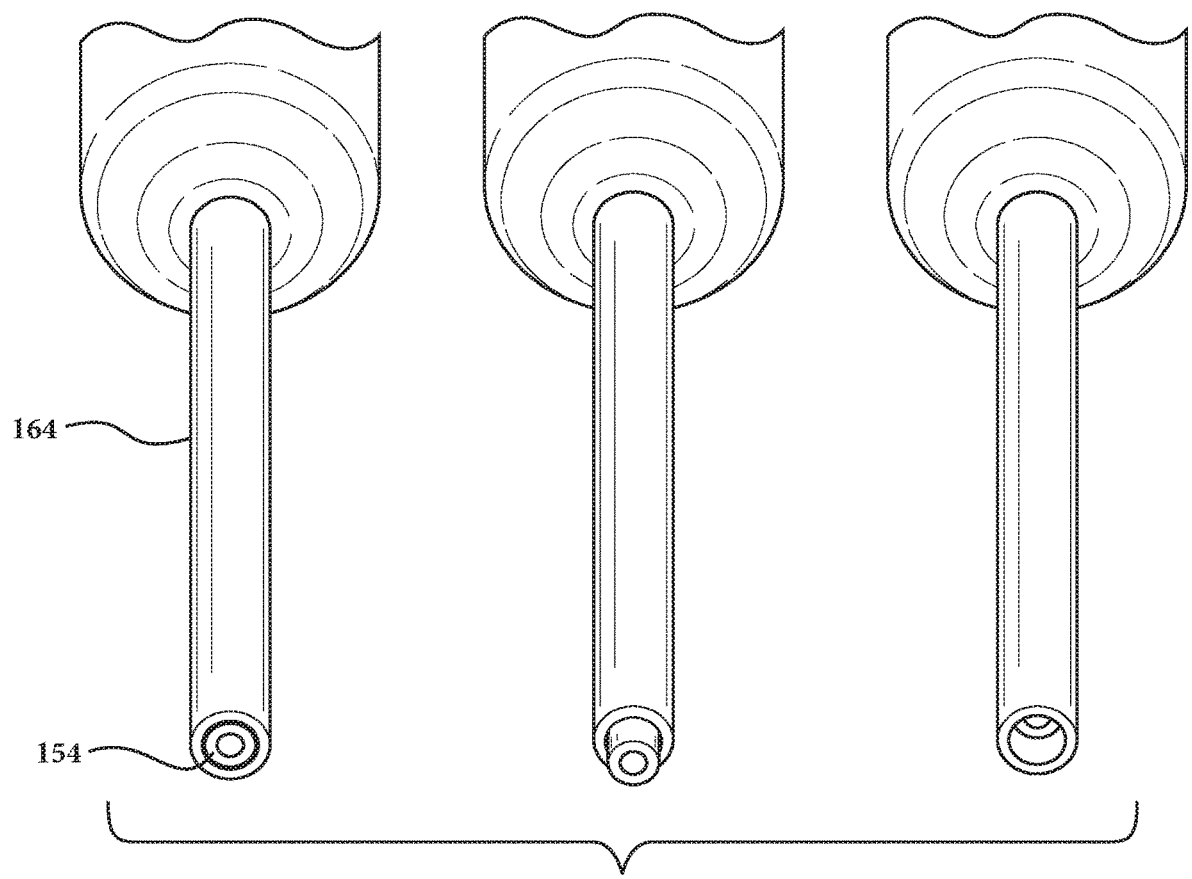
FIG. 4B is three perspective views of the needle shafts shown partially in FIG. 4A.

FIG. 4A is a side cross sectional view of the tips of the shafts 154, 164 of the shell and core needles 150, 160, in three different configurations. FIG. 4B is a perspective view of the same three configurations. In the left panel of each of FIGS. 4A and 4B, the needle shafts 154, 164 have zero offset (i.e. their tips are flush). In the middle panel, the tips have a positive offset, where the shaft 154 of the shell needle 150 protrudes from the tip of the shaft 164 of the core needle 160. In the right panel, the tips have a negative offset, where the shaft 154 of the shell needle 150 is retracted within the tip of the shaft 164 of the core needle 160.

While a zero offset will be preferred in many implementations, a positive or negative offset may be preferred in some, for example as a result of substantial viscosity disparities between core fluid and shell fluid. It will be appreciated that the needle offset can be adjusted by loosening or tightening the connection between the first and second adapter pieces 110, 120 that is mediated by the coupling of the female Luer fitting 124 of the second adapter piece 120 to the open end 113 of the internal threaded channel 112 of the first adapter piece 110. The range through which the offset is adjustable can be increased by using a thick O-ring 170 at the juncture between first and second adapter pieces 110, 120.

In certain implementations, the uncured shell fluid can include a thermally or chemically cross-linkable or photo-cross-linkable composition, such as collagen, Matrigel™, or various acrylates, alginates, or compositions thereof. The core fluid can include a different cross-linkable composition, or can include a cross-linking activator, can simply include a fluid space filler that will be removed once the shell portion is cross-linked.

It will thus be appreciated that the adapters and devices of the present teachings allow easy modification using common biomedical needles. Users thus do not have to process sharp needles in efforts to make a haphazard-makeshift device.

Nor do users have to buy expensive, pre-fabricated core-shell nozzles that are restricted to a single configuration of core and shell dimensions.

Figure 5A:
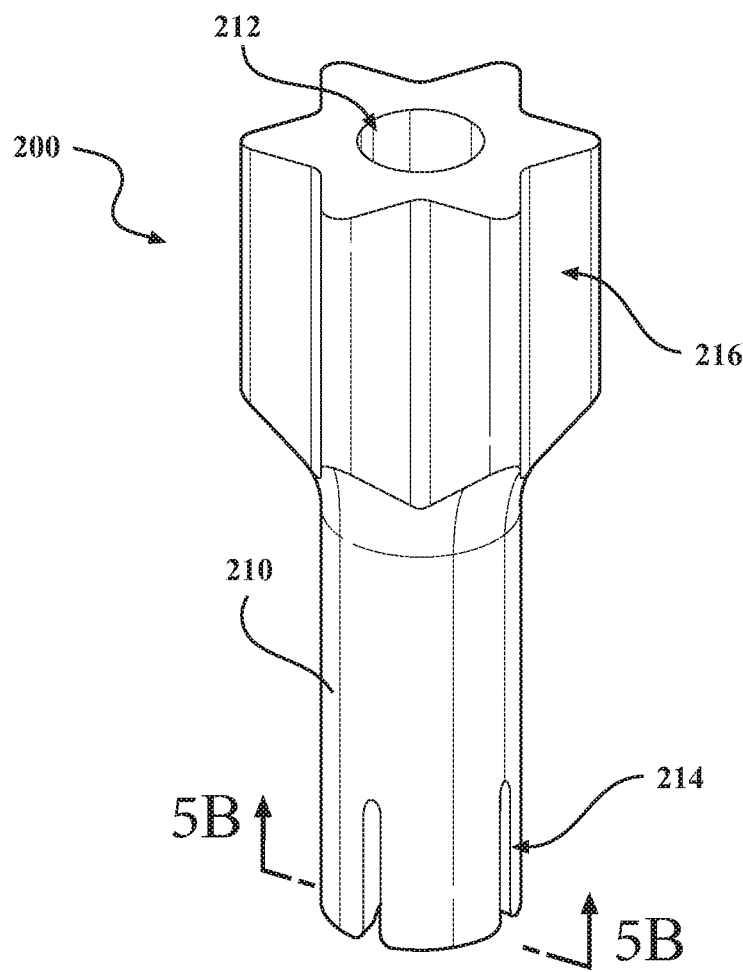
FIG. 5A is a perspective view of a tool for reversibly attaching a core needle to a first adapter piece of FIGS. 2C and 2D.
Figure 5B:
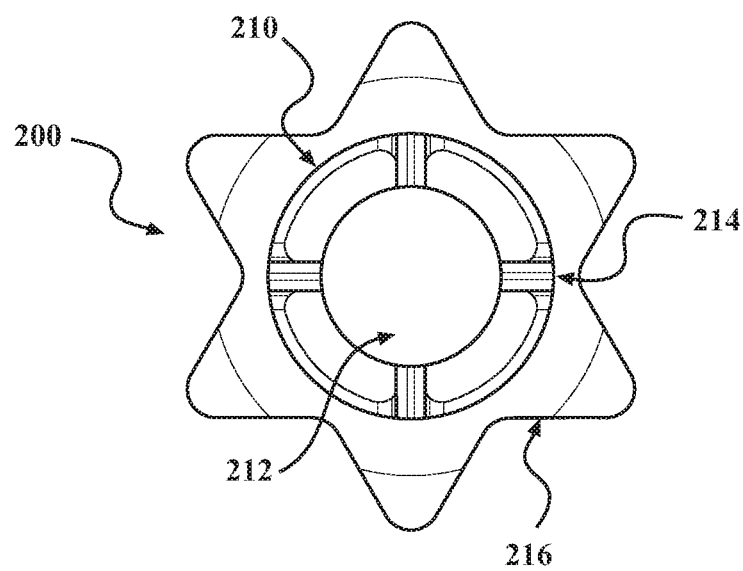
FIG. 5B is an end plan view of the tool of FIG. 5A, viewed along the line 5B-5B.

Referring again to FIGS. 2C and 2D, it will be appreciated that, in some instances, it may be difficult to manually attach a core needle 160 to a first adapter piece 110, due to the length, L, of the threaded internal channel 112. FIG. 5A shows a perspective view of a tool 200 that can facilitate attachment of the core needle 160 to the first adapter piece 110, as well as facilitating removal of the core needle 160 from the first adapter piece 110. FIG. 5B shows an end plan view of the tool 200, viewed along the line 5B-5B of FIG. 5A. The tool 200 generally includes an elongated tubular structure 210 and a through-hole 212 running the length of the tool 200 and enabling the tool to internally accommodate a core needle 160. The exemplary tool 200 of FIGS. 5A and 5B includes four notches 214 and a textured handle 216, the latter providing better manual grip of the tool 200.

Figure 6B:
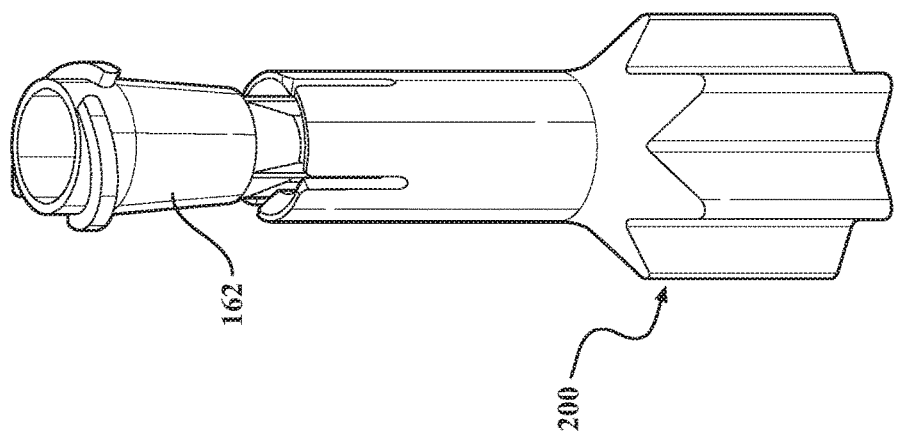
FIGS. 6A and 6B are perspective views of the tool of FIGS. 5A and 5B engaging with a core needle.
Figure 6A:
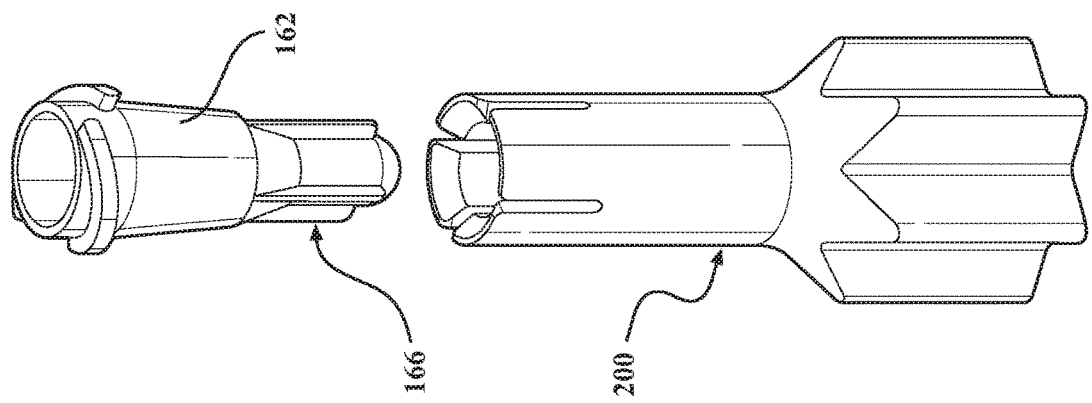

FIGS. 6A and 6B show perspective views of the tool of FIGS. 5A and 5B engaging with the hub 162 of a core needle 160. It will be understood that the hub 162 will commonly have fins 166, and thus that the notches 214 of the tool 200 are configured to mate with and grip the fins 166 of the core needle 160, so that when the tool 200 is turned like a screwdriver, the core needle 160 will turn with it. FIG. 6C shows a perspective sectional view of the tool and needle of FIG. 6B, showing the shaft 164 of core needle 160 passing through the through-hole 212 of the tool 200.

Figure 6D:
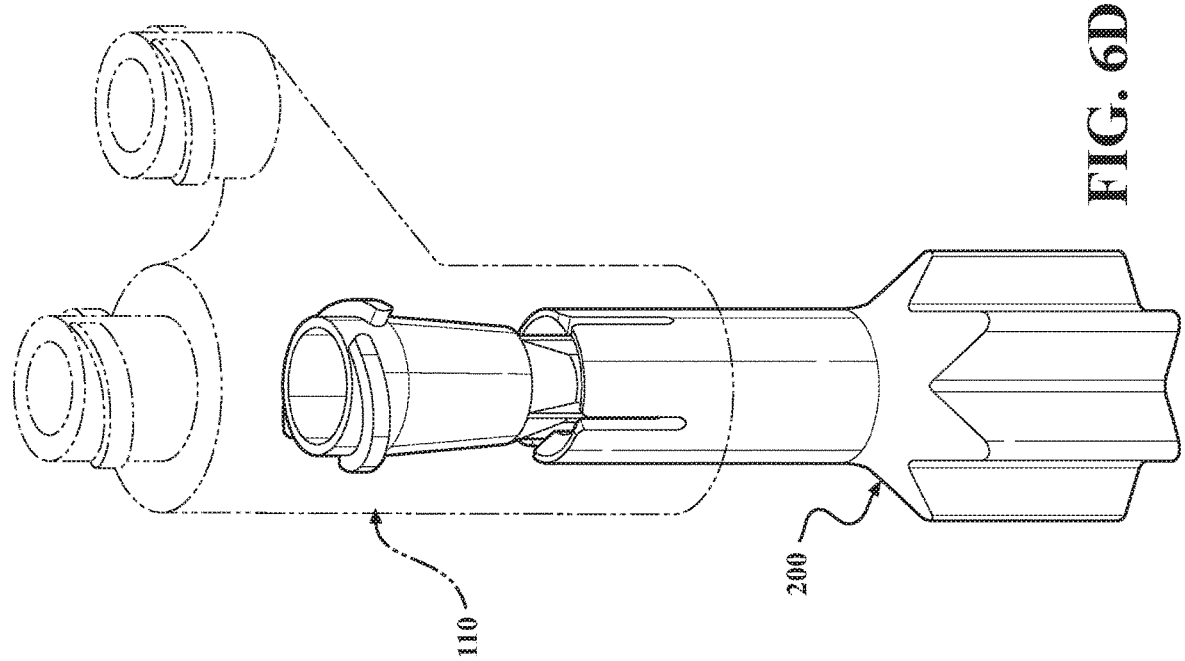
FIG. 6D is a perspective view of the tool and needle of FIG. 6B inserted into the first adapter piece of FIGS. 2C and 2D, with the first adapter piece transparent.
Figure 6C:
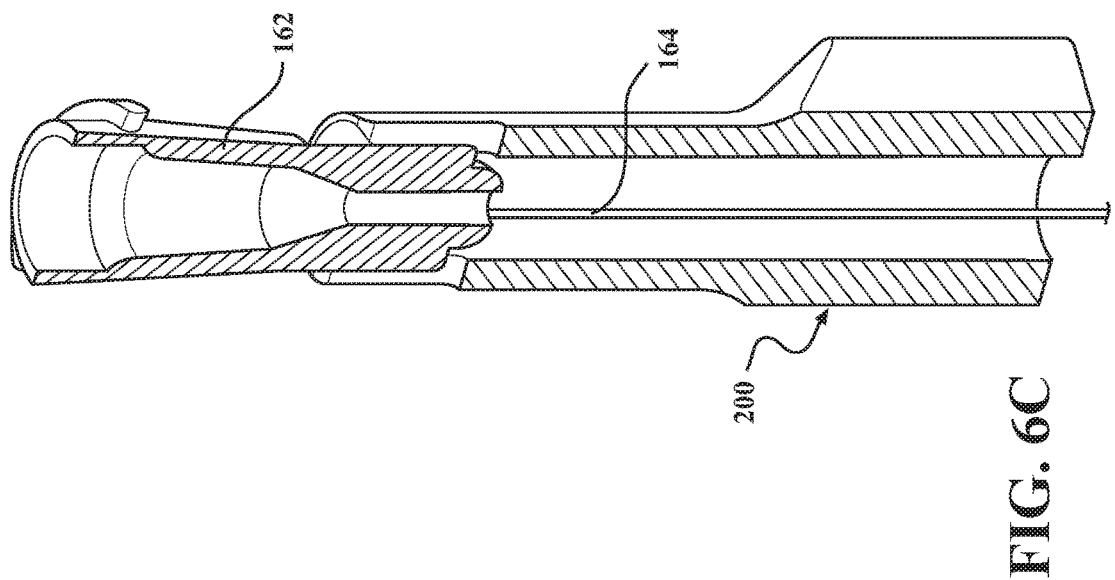
FIG. 6C is a perspective sectional view of the tool and needle of FIG. 6B.

FIG. 6D shows a perspective view of the tool and needle of FIG. 6B inserted into a first adapter piece 110, the latter rendered transparent to show the interior operation of the tool 200. It will be appreciated, with additional reference to FIG. 2C, that turning the tool 200 in this position allows a user to engage the core needle 160 with the male Luer fitting 135 of the internal threaded chamber 112 of the first adapter piece 110.

In some variations, devices 100 and adapters 105 of the present teachings can be adjusted for the extrusion of multi-layered concentric structures having more than two concentric layers (e.g. a core layer, one or more middle layers, and a shell layer). FIGS. 7A and 7B show a side plan view and a side sectional view, respectively, of a device 300 for extrusion of multi-layered concentric structures having one middle layer sitting between the core and shell layers (i.e. a core-mid-shell structure). The device 300 of FIGS. 7A and 7B is the same as the device 100 of FIGS. 1 and 2A, except that it includes first adapter piece 110A and first adapter piece 110B, stacked together. Each of first adapter piece 110A and first adapter piece 110B is the same as the first adapter piece 110 of FIGS. 1 and 2A-2D. In the device 300 of FIGS. 7A and 7B, the first inlet port of the first adapter piece 110A (equivalent to the first inlet port 130 of FIG. 2C) is a female Luer fitting that is reversibly attached to the open end of the internal threaded chamber of first adapter piece 110B (equivalent to the open end 113 of the internal threaded chamber 112 of FIG. 2C).

First adapter piece 110A is connected to core needle 160A and first adapter piece 110B is connected to mid needle 160B, as described above, so that the shaft of core needle 160B is contained inside the shaft of mid needle 160A which, in turn, is contained inside the shaft of shell needle 150, in the manner described above and shown in FIGS. 4A and 4B. It will thus be understood that uncured core fluid entering the first inlet port 130B passes into the hub and shaft of core needle 160B and is extruded as the central or core concentric layer of the multi-layer concentric structure. Uncured middle layer fluid entering the third inlet port 140B passes into the hub and shaft of mid needle 160A and is extruded as the intermediate layer of the multi-layer concentric structure. Uncured shell fluid entering the third inlet port 140A passes into the hub and shaft of shell needle 150 and is extruded as the shell or outer layer of the multi-layer concentric structure. It will be further understood that the core needle 160B should have the longest, narrowest shaft; the mid needle 160A should have a shaft of intermediate length and outer diameter; and the shell needle 150 should have the shortest, widest shaft, so that the three shafts are approximately co-terminal, as shown for two needles in FIGS. 4A and 4B.

Figure 7C:
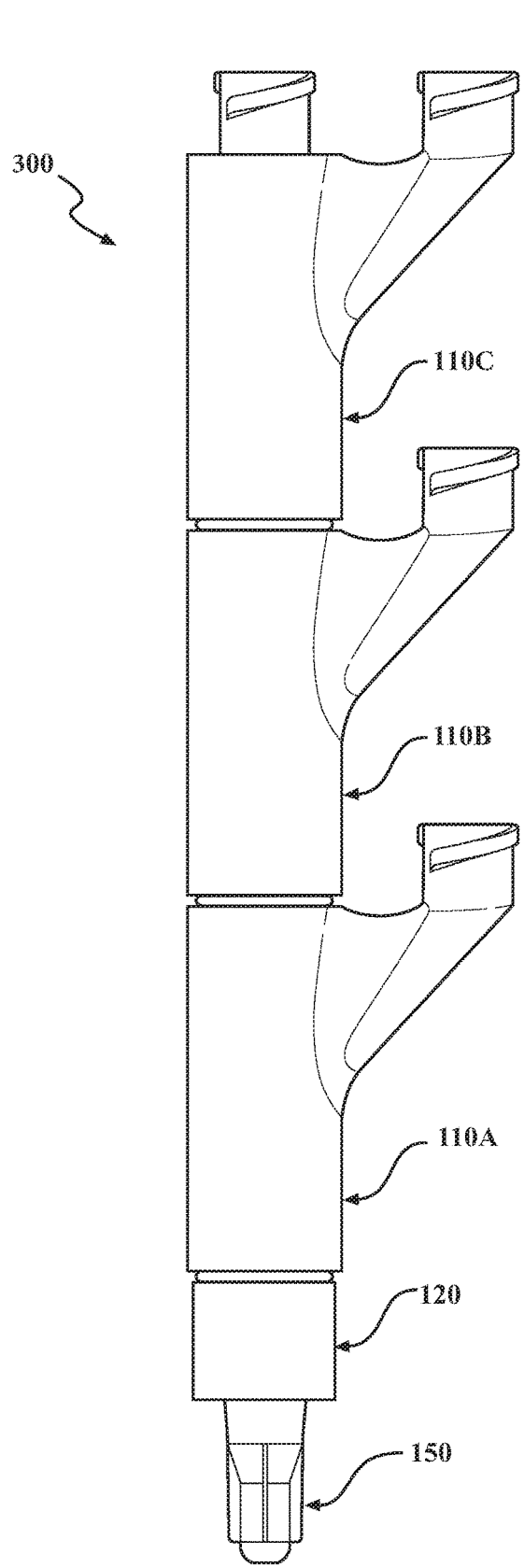
FIGS. 7C and 7D are a side plan view and a side sectional view, respectively, of an alternative variation of a device for extrusion of core-mid-mid'-shell structures, the adapter having three copies of the first adapter piece stacked to form three concentric cores.
Figure 7D:
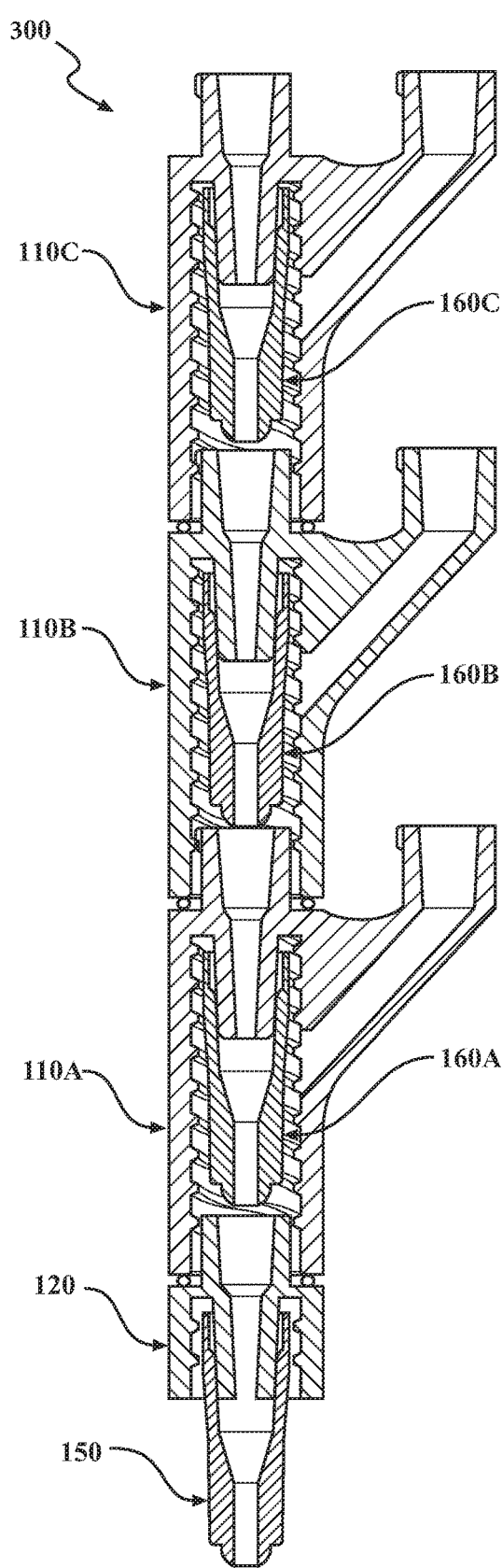

FIGS. 7C and 7D show a side plan view and a side sectional view, respectively, of a further extension of this concept, in which the device 400 for extrusion of multi-layered concentric structures having two middle layers sitting between the core and shell layers (i.e. a core-mid-mid'-shell structure). Similar to the above, uncured core fluid entering the first inlet port 130C passes into the hub and shaft of core needle 160C and is extruded as the central or core concentric layer of the multi-layer concentric structure; uncured first middle layer fluid entering the second inlet port 140C passes into the hub and shaft of mid needle 160B and is extruded as the first intermediate layer (mid) of the multi-layer concentric structure; uncured second middle layer fluid entering the third inlet port 140B passes into the hub and shaft of mid needle 160A and is extruded as the second intermediate layer (mid') of the multi-layer concentric structure; and uncured shell fluid entering the fourth inlet port 140A passes into the hub and shaft of shell needle 150 and is extruded as the shell or outer layer of the multi-layer concentric structure. It will be appreciated that only limit on the number of intermediate layers that can be added is in the availability of needles that can be concentrically inserted in one another.

It will be understood that, while Luer fittings are generally preferred for their commonality and direct use with most needles, the various male and female Luer fittings of the present adapters and devices can be replaced with other connection types. It is preferable that such connections be reasonably standardized or standardizable, and applicable to needle connections. It will be further understood that the first and second adapter pieces 110, 120 can be formed of plastic, metal, or any other relatively hard, inflexible material applicable to Luer fittings.

The preceding description is merely illustrative in nature and is in no way intended to limit the disclosure, its application, or uses. As used herein, the phrase at least one of A, B, and C should be construed to mean a logical (A or B or C), using a non-exclusive logical "or." It should be understood that the various steps within a method may be executed in different order without altering the principles of the present disclosure. Disclosure of ranges includes disclosure of all ranges and subdivided ranges within the entire range.

The headings (such as "Background" and "Summary") and sub-headings used herein are intended only for general organization of topics within the present disclosure, and are not intended to limit the disclosure of the technology or any aspect thereof. The recitation of multiple embodiments having stated features is not intended to exclude other embodiments having additional features, or other embodiments incorporating different combinations of the stated features.

As used herein, the terms "comprise" and "include" and their variants are intended to be non-limiting, such that recitation of items in succession or a list is not to the exclusion of other like items that may also be useful in the devices and methods of this technology. Similarly, the terms "can" and "may" and their variants are intended to be non-limiting, such that recitation that an embodiment can or may comprise certain elements or features does not exclude other embodiments of the present technology that do not contain those elements or features.

The broad teachings of the present disclosure can be implemented in a variety of forms. Therefore, while this disclosure includes particular examples, the true scope of the disclosure should not be so limited since other modifications will become apparent to the skilled practitioner upon a study of the specification and the following claims. Reference herein to one aspect, or various aspects means that a particular feature, structure, or characteristic described in connection with an embodiment or particular system is included in at least one embodiment or aspect. The appearances of the phrase "in one aspect" (or variations thereof) are not necessarily referring to the same aspect or embodiment. It should be also understood that the various method steps discussed herein do not have to be carried out in the same order as depicted, and not each method step is required in each aspect or embodiment.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations should not be regarded as a departure from the disclosure, and all such modifications are intended to be included within the scope of the disclosure.

What is claimed is:

1. An adapter for extruding core-shell structures with two needles, the adapter comprising:
    a first adapter piece comprising:
        a body having an internal threaded chamber with first and second opposite ends, the first opposite end comprising an open threaded end configured to couple with a female Luer fitting, and the second opposite end comprising an internal male Luer fitting, and a first inlet port with a first inlet female Luer fitting configured to pass a first inlet fluid directly to the internal male Luer fitting; and
        a second inlet port configured to pass a second inlet fluid into the internal threaded chamber via a side channel; and
    a second adapter piece comprising:
        a second female Luer fitting configured to couple with the open threaded end of the internal threaded chamber; and
        a male Luer fitting configured to couple with a needle, the male Luer fitting extending coaxially from the female Luer fitting.

2. The adapter as recited in claim 1, wherein the second adapter piece is reversibly connected to the first adapter piece via connection of the second female Luer fitting to the internal threaded chamber.

3. The adapter as recited in claim 2, further comprising an O-ring positioned between the first and second adapter pieces.

4. The adapter as recited in claim 1, comprising Luer tube fittings reversibly connected to the first and second inlet ports.

5. The adapter as recited in claim 1, formed of a thermoplastic.

6. A device for extruding core-shell tubular structures, the device comprising:
    a core fluid pathway comprising:
        a first inlet port with a core inlet female Luer fitting, the first inlet port being on a first adapter piece and configured to receive core fluid from an external source;
        a first tapered male Luer fitting on the first adapter piece in direct fluid communication with the core inlet female Luer fitting of the first inlet port; and
        a core needle attached to the first tapered male Luer fitting and in fluid communication with the first inlet port;
    a shell fluid pathway comprising:
        a cylinder with a threaded internal chamber surrounding the first tapered male Luer fitting;
        a side channel in the first adapter piece, connected to an aperture in the threaded internal chamber;
        a second inlet port atop the side channel;
    a second adapter body having:
        a second adapter body female Luer fitting, reversibly attached to the threaded internal chamber;
        a second tapered male Luer fitting in direct fluid communication with the second adapter body female Luer fitting; and
        a shell needle connected to the second tapered male Luer fitting, and in fluid communication with the second inlet port, such that the core and shell needles are coaxial.

7. The device as recited in claim 6, wherein the core needle comprises a core needle shaft having an outer diameter, the shell needle comprises a shell needle shaft having an inner diameter that is greater than the outer diameter of the core needle shaft.

8. The device as recited in claim 7, wherein the core needle shaft is positioned inside the shell needle shaft.

9. The device as recited in claim 6, wherein the second inlet port comprises a tube fitting.

10. The device as recited in claim 6, wherein the second inlet port comprises a shell inlet female Luer fitting.

11. The device as recited in claim 10, wherein the shell inlet female Luer fitting is a reversibly connected shell inlet female Luer fitting.

12. The device as recited in claim 10, wherein the first female Luer fitting is a core inlet female Luer fitting, the second inlet port comprises a shell inlet female Luer fitting; and further comprising:
    a core fluid syringe reversibly attached to the core inlet female Luer fitting; and
    a shell fluid syringe reversibly attached to the shell inlet female Luer fitting.

13. The device as recited in claim 12, wherein the core fluid syringe comprises a core fluid, and the shell fluid syringe comprises an uncured shell fluid.

14. The device as recited in claim 13, wherein the uncured shell fluid comprises at least one material selected from the group consisting of:
    a photopolymerizable species;
    a thermal cross-linkable species;
    a chemical cross-linkable species; and
    a photocross-linkable species.

15. The device as recited in claim 6, further comprising a tool for removing or re-attaching the core needle to the first tapered male Luer fitting, the tool comprising:

an elongated tubular structure;

a through-hole running internally through a length of the elongated tubular structure, and enabling the tool to internally accommodate a shaft of the core needle; and notches in an end of the elongated tubular structure, the notches configured to mate with and grip fins in a hub of the core needle.

16. A device for extruding multi-layered concentric structures with three or more needles, the device comprising:

a first adapter piece comprising:

a body having an internal threaded chamber with first and second opposite ends, the first opposite end comprising an open end configured to couple with a female Luer fitting, and the second opposite end comprising an internal male Luer fitting, and a first inlet port with a first inlet female Luer fitting configured to pass a first inlet fluid directly to the internal male Luer fitting; and a second inlet port configured to pass a second inlet fluid into the internal threaded chamber via a side channel;

a second adapter piece comprising:

a second adapter piece female Luer fitting configured to couple with the open end of the internal threaded chamber; and a male Luer fitting configured to couple with a needle, the male Luer fitting extending coaxially from the female Luer fitting; and an additional adapter piece substantially identical to the first adapter piece and comprising:

a body having an internal threaded chamber with first and second opposite ends, the first opposite end comprising an open end configured to couple with the second adapter piece female Luer fitting of the second adapter piece, and the second opposite end comprising an internal male Luer fitting, and a first inlet port comprising an external female Luer fitting configured to couple with the open end of the first adapter piece; and a third inlet port configured to pass a third inlet fluid into the internal threaded chamber via a side channel;

a core needle connected to the internal male Luer fitting of the first adapter piece;

a mid needle connected to the internal male Luer fitting of the additional adapter piece; and a shell needle connected to the male Luer fitting of the second adapter piece.

17. The device as recited in claim 16, wherein the core needle comprises a core needle shaft having an outer diameter; the mid needle comprises a mid needle shaft having an inner diameter that is greater than the outer diameter of the core needle shaft, and having an outer diameter; and the shell needle comprises a shell needle shaft having an inner diameter that is greater than the outer diameter of the mid needle shaft.

18. The device as recited in claim 17, wherein the core needle shaft is positioned inside the mid needle shaft, which is positioned inside the shell needle shaft.

19. The device as recited in claim 17, wherein the relative positions of the core needle shaft, the mid needle shaft, and the shell needle shaft are characterized by an offset, the offset being manually adjustable by loosening or tightening at least one connection between the first, second, and additional adapter pieces.

20. The device as recited in claim 16, wherein the first inlet female Luer fitting is a core inlet female Luer fitting, the second inlet port comprises a shell inlet female Luer fitting; and further comprising:

a core fluid syringe reversibly attached to the core inlet female Luer fitting; and a shell fluid syringe reversibly attached to the shell inlet female Luer fitting.

* * * * *